United States Patent
Napoletano et al.

(10) Patent No.: US 6,525,055 B1
(45) Date of Patent: Feb. 25, 2003

(54) TRICYCLIC PHTHALAZINE DERIVATIVES AS PHOSPHODIESTERASE 4 INHIBITORS

(75) Inventors: Mauro Napoletano, Milan (IT); Gabriele Norcini, Vizzola Ticino (IT); Franco Pellacini, Milan (IT); Gabriele Morazzoni, Lainate (IT)

(73) Assignee: Zambon Group S.p.A., Vicenza (IT)

( * ) Notice: Subject to any disclaimer, the term of this patent is extended or adjusted under 35 U.S.C. 154(b) by 0 days.

(21) Appl. No.: 09/830,679

(22) PCT Filed: Oct. 1, 1999

(86) PCT No.: PCT/EP99/07304

§ 371 (c)(1),
(2), (4) Date: Apr. 30, 2001

(87) PCT Pub. No.: WO00/26218

PCT Pub. Date: May 11, 2000

(30) Foreign Application Priority Data

Oct. 29, 1998 (IT) ............................................ MI98A2319

(51) Int. Cl.⁷ ................... A61K 31/5025; C07D 487/04; C07D 237/00; C07D 257/00; C07D 249/00
(52) U.S. Cl. ........................................ 514/248; 544/234
(58) Field of Search ............................ 544/234; 514/248

(56) References Cited

U.S. PATENT DOCUMENTS

| | | | |
|---|---|---|---|
| 3,704,300 A | * 11/1972 | Hardtmann | .................. 544/234 |
| 4,783,461 A | * 11/1988 | Occelli et al. | .............. 544/234 |
| 6,313,125 B1 | * 11/2001 | Carlng et al. | .............. 544/234 |

FOREIGN PATENT DOCUMENTS

| | | |
|---|---|---|
| DE | 196 17 862 | 10/1997 |
| EP | 0 548 923 | 6/1993 |
| EP | 0 620 224 | 10/1994 |
| EP | 0 722 936 | 7/1996 |
| WO | WO 93/07146 | 4/1993 |
| WO | WO 98/04559 | 2/1998 |
| WO | WO 98/07430 | 2/1998 |
| WO | WO 98/21208 | 5/1998 |
| WO | WO 99/32456 | 7/1999 |

OTHER PUBLICATIONS

V. D. Piaz, et al., "Novel Heterocyclic–Fused Pyridazinones as Potent and Selective Phosphodiesterase IV Inhibitors", J. Med. Chem., vol. 40, No. 10, 1997, pp. 1417–1421.

* cited by examiner

Primary Examiner—Richard L. Raymond
(74) Attorney, Agent, or Firm—Oblon, Spivak, McClelland, Maier & Neustadt, P.C.

(57) ABSTRACT

Tricyclic phthalazine compounds of formula (I)

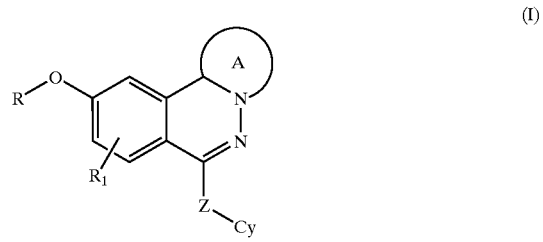

wherein A is a 5–7 membered heterocycle containing from 1 to 4 nitrogen atoms, optionally partially or totally unsaturated, and optionally substituted by a $(C_{1-4})$alkyl group in turn optionally substituted; Z is NH, methylene, a $C_{2-6}$ alkylene chain optionally branched and/or unsaturated and/or interrupted by a $C_{5-7}$ cycloalkyl residue; Cy is phenyl or heterocycle optionally substituted by one or more substituents, or a $COR_4$ group wherein $R_4$ is hydroxy, alkoxy, amino optionally substituted by one or two $(C_{1-6})$ alkyl groups or by hydroxy; R is a $(C_{1-6})$alkyl or polyfluoro $(C_{1-6})$alkyl group; $R_1$ is hydrogen; a $(C_{1-8})$-alkyl, $(C_{2-8})$-alkenyl or $(C_{2-8})$-alkynyl group optionally substituted by hydroxy, oxo, aryl or heterocycle, and optionally interrupted by one or more heteroatoms or heterogroups; a $(C_{1-4})$alkoxy group or a $(C_{4-7})$cycloalkoxy group optionally containing an oxygen atom and optionally substituted by a polar substituent in the cyclic moiety, aryloxy aryl-$(C_{1-10})$-alkoxy; the N—O derivatives and the pharmaceutically acceptable salts thereof are described. The compounds of formula (I) are PDE 4 inhibitors.

13 Claims, No Drawings

TRICYCLIC PHTHALAZINE DERIVATIVES AS PHOSPHODIESTERASE 4 INHIBITORS

This application is a 371 of PCT/EP99/07304, filed Oct. 1, 1999.

The present invention relates to tricyclic derivatives, to the pharmaceutical compositions containing them and to their use as phosphodiesterase 4 inhibitors.

Phosphodiesterases are a family of isoenzymes which constitute the basis of the main mechanism of cAMP (cyclic adenosine-3',5'-monophosphate) hydrolytic inactivation. cAMP has been shown to be the second messenger mediating the biologic response to many of hormones, neurotransmitters and drugs [Krebs Endocrinology Proceedings of the 4th International Congress Excerpta Medica, 17–29, 1973]. When the suitable agonist binds to the cell surface, the adenylated cyclase activates and turns $Mg^{2+}$-ATP into cAMP. cAMP modulates the activity of the majority, if not of all the cells contributing to the pathophysiology of various respiratory diseases, both of allergic origin and not. It follows that an increase of the cAMP concentration yields beneficial effects such as airway smooth muscle relaxation, inhibition of the mast cell mediator release (basophil granulose cells), suppression of the neutrophil and basophil degranulation, inhibition of the monocyte and macrophage activation. Thus, compounds able of activating adenylate cyclase or of inhibiting phosphodiesterases could suppress the undesired activation of the airway smooth muscle and of a great number of inflammatory cells.

In the phosphodiesterase family there is a distinct group of isoenzymes, phosphodiesterases 4 (hereinafter PDE 4) specific for the cAMP hydrolysis in the airway smooth muscle and inflammatory cells (Torphy, "Phosphodiesterase Isoenzymes: Potential Targets for Novel Anti-asthmatic Agents" in New Drugs for Asthma, Barnes, ed. IBC Technical Services Ltd. 1989). Studies carried out on this enzyme show that its inhibition yields not only the airway smooth muscle relaxation, but also the suppression of mastocyte, basophil and neutrophil degranulation, so as the inhibition of the monocyte and neutrophil activation. In addition, the action of PDE 4 inhibitors is markedly strengthened when the adenylate cyclase activity of the target cells is increased by endogenous hormones, as it happens in vivo. Thus PDE 4 inhibitors are effective in the therapy of asthma. Such compounds offer a unique approach to the therapy of various respiratory diseases, both of allergic origin and not, and possess significant therapeutic advantages over the current therapy.

The excessive or irregular production of tumour necrosis factor (hereinafter $TNF_\alpha$), a cytokine with pro-inflammatory activity produced by various kinds of cells, affects the mediation or the exacerbation of many pathologies such as, for example, the adult respiratory distress syndrome (ARDS) and the chronic pulmonary inflammatory disease. Therefore compounds able to control the negative effects of $TNF_\alpha$, i.e. the inhibitors of this cytokine, are to be considered as useful against many pathologies.

The patent EP 0 526 840 (iKyowa Hakko Kogyo) claims compounds of formula

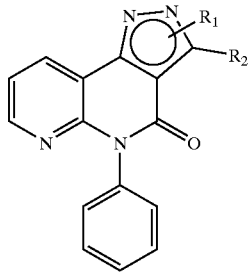

wherein $R_1$ is hydrogen, $(C_{1-6})$alkyl, $(C_{7-15})$arylalkyl or optionally substituted aryl; and $R_2$ is hydrogen, $(C_{1-6})$alkyl, thienyl or optionally substituted aryl. These compounds are said to be active, inter alia, as antiinflammatories, immunosuppressives, bronchodilators.

The patent application JP 09227563 (Lederle Japan) describes compounds of formula

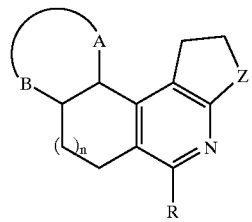

wherein R is an optionally substituted amino group, Z is S or O, A and B form a benzene ring or are absent, and n is 0–2. These compounds are useful as bronchodilators, antiasthmatics, antihypertensives and anticholesterolemics.

The patent application WO 97/34893 (Astra) describes compounds of formula

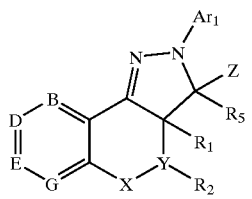

wherein B, D, E and G may form a benzene ring optionally substituted by alkoxy; X is C=O, C=S, C=NR, $CR_3R_6$ or $NR_4$; $R_3$ is H or forms a bond with $R_2$; $R_4$ is lower alkyl or forms a bond with $R_2$; $R_6$ may be H, lower alkyl optionally substituted by phenyl, or cycloalkyl, phenyl, etc.; Y is N or CR; $R_2$ may be H, lower alkyl optionally substituted by phenyl COOR, NR'R", OR, F, or cycloalkyl or may form a bond with one of $R_1$, $R_3$ and $R_4$; $R_1$ may be OH or lower alkyl or may form a bond with one of $R_2$ and $R_5$; $R_5$ is a bond with $R_1$ or $R_8$; Z is $OR_8$ or O; and $Ar_1$ may be optionally substituted phenyl, pyridyl, pyrimidyl. These compounds have an antiinflammatory activity.

The patent application WO 98/09969 (Astra) describes compounds of formula

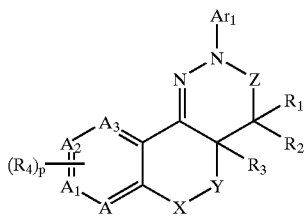

wherein A, $A_1$, $A_2$ and $A_3$ may be CH or $CR_4$, X may be $CH_2$ or O; Y may be a bond, $CH_2$, C=O, C substituted by alkyl in turn substituted by a cyclic residue; Z is a bond or $CH_2$; $R_1$ is hydrogen, lower alkyl or alkoxy; $R_2$ and $R_3$ are hydrogen or form a bond; and $R_4$ may be optionally substituted alkoxy. These compounds have an antiinflammatory and antiallergic activity.

The patent application DE 19617862 (Schering AG) describes compounds of formula

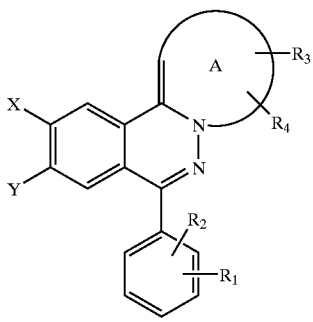

wherein, inter alia, $R_1$ and $R_2$ are H, alkyl, nitro, halogen, amino, lower alkoxy, $CF_3$; $R_3$ and $R_4$ are H, alkyl, aryl, heteroaryl or cycloalkyl; X=H; Y is alkoxy or X+Y=—O—$(CH_2)_n$—O—; n=1–3; and A is a 5-member heterocycle having from 1–3 nitrogen atoms. These compounds are inhibitors of glutamate receptor.

The patent application EP 0 548 923 (Takeda Chemical Ind.) describes, inter alia, compounds of formula

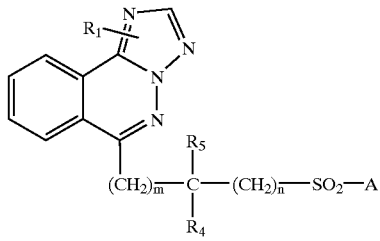

wherein $R_1$ is H or a lower alkyl group or a halogen atom; $R_4$ and $R_5$ are H or a lower alkyl group or form a 3–7 membered cycle optionally containing a heteroatom together with the carbon atom to which they are bound; A is an optionally substituted amino group: and m, n=1–4. These compounds are antiallergics, antiinflammatories and anti-PAF (anti-piastrinic activating factor), and are useful as antiasthmatics. In fact, these compounds act through an anti-PAF mechanism which makes them bronchodilators.

Similar compounds are claimed in the patent application EP 0 620 224 (Takeda Chemical Ind.) which illustrates, inter alia, the general formula

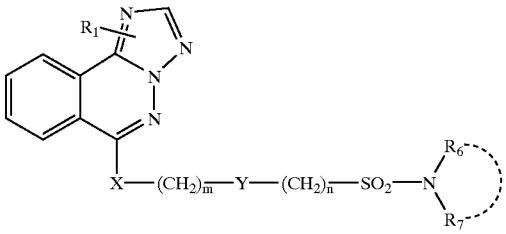

wherein $R_1$ is H or a lower alkyl group or a halogen atom; X is an oxygen or sulphur atom or a —$CH_2$— group; Y is a group

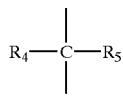

wherein $R_4$ and $R_5$ are H or a lower alkyl group, or is a 3–7 membered cycle optionally containing a heteroatom; $R_6$ and $R_7$ are H, an optionally substituted lower alkyl, cycloalkyl or aryl or together with the nitrogen atom to which they are bound form a heterocycle, and m, n=0–4. These compounds have the same activity claimed in the just above cited patent application.

The patent application WO 98/21208 (Byk Gulden Lomberg) claims PDE3 and PDE4 inhibitors of formula

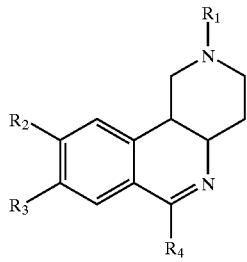

wherein, inter alia, $R_1$ is an alkyl group; $R_2$ and $R_3$ are hydroxy, optionally fluorinated alkoxy, cycloalkoxy and cycloalkylmethoxy; and $R_4$ is a phenyl group substituted by carboxy, amido or alkoxycarbonyl and optionally substituted by halogen, alkyl, $CF_3$, nitro or hydroxy. These compounds are said to be useful in the treatment of pathologies of the airways and/or of dermatosis.

It has now surprisingly been found a new class of phthalazine derivatives able to inhibit PDE 4 and $TNF_\alpha$.

Therefore the present invention relates to compounds of formula (I)

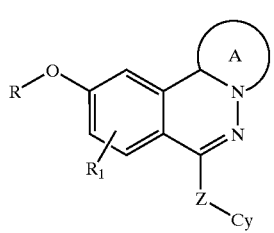

wherein

A is a 5–7 membered heterocycle containing from 1 to 4 nitrogen atoms, optionally partially or totally unsaturated, and optionally substituted by a (C₁₋₄)alkyl group in turn optionally substituted;

Z is NH, methylene, a C₂₋₆ alkylene chain optionally branched and/or unsaturated and/or interrupted by a C₅₋₇ cycloalkyl residue;

Cy is phenyl or heterocycle optionally substituted by one or more substituents, or a COR₄ group wherein R₄ is hydroxy, alkoxy, amino optionally substituted by one or two (C₁₋₆)alkyl groups or by hydroxy;

R is a (C₁₋₆)alkyl or polyfluoro(C₁₋₆)alkyl group;

R₁ is hydrogen; a (C₁₋₈)-alkyl, (C₂₋₈)-alkenyl or (C₂₋₈)-alkynyl group optionally substituted by hydroxy, oxo, aryl or heterocycle, and optionally interrupted by one or more heteroatoms or heterogroups; a (C₁₋₄)alkoxy group or a (C₄₋₇)cycloalkoxy group optionally containing an oxygen atom and optionally substituted by a polar substituent in the cyclic moiety, aryloxy, aryl-(C₁₋₁₀)-alkoxy;

the N→O derivatives of the compounds of formula I and the pharmaceutically acceptable salts thereof.

Preferred compounds according to the invention are those of formula I wherein Z is methylene or a C₂₋₆ alkylene chain.

Still more preferred compounds according to the invention are those of formula I wherein Z is methylene or a C₂₋₆ alkylene chain; and Cy is a heterocycle optionally substituted by one or more substituents.

Still more preferred compounds according to the invention are those of formula I wherein Z is methylene; and Cy is pyridine substituted by two substituents.

The compounds of formula I can have one or more asymmetric centres and therefore they can be in the form of stereoisomers. Object of the present invention are compounds of formula I in the form of diastereoisomeric mixtures as well as of single stereoisomers.

The compounds of formula I are active as PDE 4 and TNFα inhibitors and thus are used as therapeutic agents in allergic and inflammatory pathologies such as, for example, emphysema, chronic bronchitis, asthma and allergic rhinitis.

For substituent Cy, as heterocycle it is particularly meant pyrrole, imidazole, pyrazole, pyridine, pyrazine, pyrimidine, pyridazine, piperazine, triazine, morpholine, pyrrolidine, pyrroline, imidazoline, pyrazoline, pyrazolidine, imidazolidine, piperidine, furan, pyran, isothiazole, isoxazole, thiophene and the like.

The optionally present substituents can be oxo, nitro, carboxy, halogen, that means a fluorine, chlorine, bromine or iodine atom. As "polar substituent" they are meant those groups made by atoms having a different electronegativity, so forming a dipole, such as, for example, a hydroxy or keto group.

Specific examples of alkyl groups are methyl, ethyl, n-propyl, i-propyl, n-butyl, s-butyl, t-butyl, n-pentyl, 1-methyl-butyl, 2-ethyl-propyl, 3-methyl-butyl, 3-methyl-2-butyl, n-hexyl, heptyl, octyl and the like; examples of substituents optionally present on the alkyl groups are (C₁₋₆)alkoxy groups and amino groups mono- or di-substituted by (C₁₋₄)alkyl groups.

As (C₄₋₇)cycloalkyl group cyclobutyl, cyclopentyl, cyclohexyl and cycloheptyl are meant, while the aryl and the aryl moiety of the aryl-(C₁₋₁₀)alkyl substituent mean an aromatic ring of 6–10 carbon atoms such as, for example, phenyl, naphthyl, indanyl, and the like, and, consequently, as aryl-(C₁₋₁₀)-alkyl substituent, benzyl, phenylethyl, phenylpentyl, indanyl-pentyl and the like.

The oxidised form N→O, when present, can be on the nitrogen atoms of the phthalazine ring as well as on those on Cy.

Pharmaceutically acceptable salts of the compounds of formula I are those with organic and inorganic acids, such as, for example, hydrochloric, hydrobromic, hydroiodic, sulfulric, phosphoric, nitric, acetic, benzoic, maleic, fumaric, succinic, tartaric, citric, aspartic, methanesulfonic and 3,7-di-t.butylnaphthalen-1,5-disulfonic (dibudinic acid), or with inorganic bases such as, for example, sodium or potassium hydroxide, sodium bicarbonate.

The synthesis of the compounds of formula I proceeds according to methods known to the skilled in the art. For example, when a compound of formula I wherein Z is different from NH is desired, the synthesis can start from an acid of formula

(II)

wherein R and R₁ are as above defined, which by reaction with formaldehyde/HCl gives a compound of formula

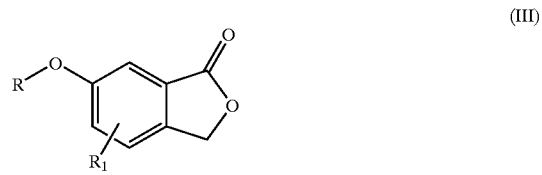

(III)

wherein R and R₁ are as above defined. This is oxidised, for example, with benzoyl peroxide/N-bromo-succinimide, and then hydrolysed to give a compound of formula

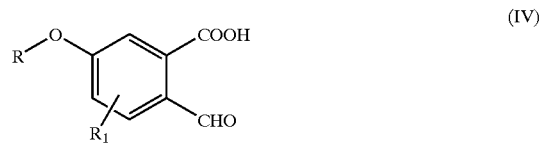

(IV)

wherein R and R₁ are as above defined, which is treated with a hydrohalogenidric acid (HX) and triphenylphosphine to give a compound of formula

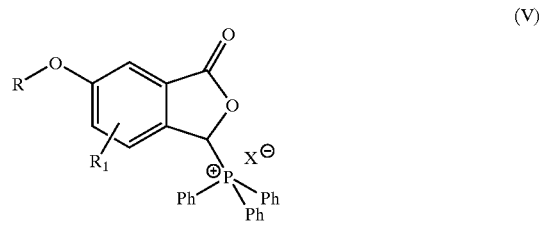

(V)

wherein R and R₁ are as above defined. This compound can be also obtained from compound III by radicalic halogenation with, for example, azaisobutyronitrile or benzoyl peroxide/N-bromo- or chloro-succinimide to give the compound of formula

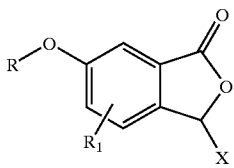

(IIIa)

wherein R and $R_1$ are as above defined, and X is chlorine or bromine, which gives compound V by treatment with triphenylphosphine.

Compound V is treated with an aldheyde of formula

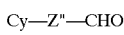

Cy—Z"—CHO  (VI)

wherein Cy is as above defined and Z" is a $C_{1-5}$ alkylene chain optionally branched and/or unsaturated and/or interrupted by a $C_{5-7}$ cycloalkyl residue, or it is absent, in the presence of an organic base such as, for example, triethylamine, and gives a compound of formula

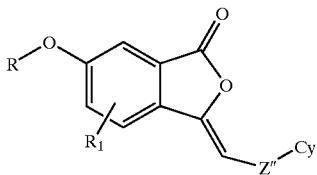

(VII)

wherein R, $R_1$, Z" and Cy are as above defined. This is reacted with hydrazine to give a compound of formula

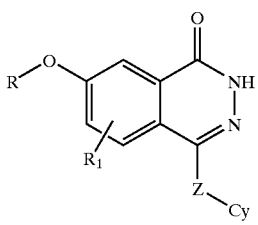

(VIII)

wherein R, $R_1$, and Cy are as above defined and Z has the meanings reported in formula I but amino, which is treated with a halogenating agent, such as phosphoryl chloride or bromide, to give a compound of formula

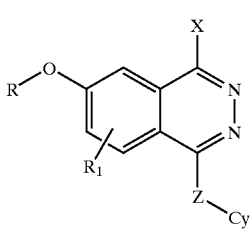

(IX)

wherein R, $R_1$ and Cy are as above defined, X is chlorine or bromine, and Z is different from amino, which is treated with a suitable nucleophile such as, for example, sodium azide or sodium tetrazolate, or with hydrazine and then with a suitable acylating agent such as, for example, acetic anhydride or acetyl chloride, and gives the desired compound of formula I.

The synthesis of the N-oxides of the compounds of formula I occurs by treating the compounds of formula I with peracids such as, for example, m-chloroperbenzoic acid.

The preparation of the salts of the compounds of formula I is carried out according to conventional methods.

The compounds of formula I are PDE 4 inhibitors as showed by the in vitro enzymatic inhibition tests (example 18), and furthermore are able to inhibit the $TNF_\alpha$ release.

It is apparent how these enzymatic selectivity and specificity features combined with the lack of activity on the cardiovascular system make the compounds of formula I specifically suitable for treating pathologies involving PDE 4 and $TNF_\alpha$ even if in the present context the interest is particularly focused on the respiratory pathologies. In particular the compounds of the invention are useful for treating allergic and inflammatory diseases and above all for treating emphysema chronic obstructive pulmonary disease (COPD) and chronic bronchitis specifically, asthma and allergic rhinithis.

The therapeutic doses shall be generally from 0.1 to 1.000 mg a day and from 1 to 100 mg by oral route for single administration.

A further object of the present invention are the pharmaceutical compositions containing a therapeutically effective amount of the compounds of formula I or pharmaceutically acceptable salts thereof in admixture with a suitable carrier.

The pharmaceutical compositions object of the invention can be liquid, suitable for the enteral or parenteral administration, and, preferably, solid such as tablets, capsules, granulates, suitable for the oral administration, or in a form suitable for the transdermal and inhalatory administration.

The preparation of the pharmaceutical compositions object of the invention can be carried out according to common techniques.

In order to better illustrate the invention the following examples are now given.

The $^1$H-NMR spectra were run at 200 MHz, δ are in parts per million.

EXAMPLE 1

5,6-Dimethoxy-3H-isobenzofuran-1-one

A suspension of 3,4-dimethoxy-benzoic acid (353.5 g, 1.94 moles) in HCHO (1.7 l, 24.5 moles) was prepared under mechanic stirring, cooled in ice, saturated with gaseous HCl (340 g, 9.32 moles), then gradually brought to 60° C. After one night the temperature was brought to the room values and further HCl (300 mg) was bubbled, then the temperature was brought again to 60° C. for one night. The mixture was brought to small volume, taken up with water (1 l), neutralised with 28% $NH_4OH$ (1.5 l) and kept at cool for 2 hours, then filtered. The filtrate was washed with water up to neutrality, then crystallised from $CH_3OH$ (2 l) and dried under vacuum at 60° C. to give 220 g of the title compound (yield: 58.65%).

$^1$H-NMR (CDCl$_3$): 7.28 and 6.28 (2s, 2H); 5.20 (s, 2H); 3.95 and 3.91 (2s, 6H).

EXAMPLE 2

2-Formyl-4,5-dimethoxy-benzoic acid

A mixture of 5,6-dimethoxy-3H-isobenzofuran-1-one (10 g, 51.5 mmoles), obtained as described in example 1, under $N_2$ in CCl$_4$ (250 ml), N-bromo-succinimide (13.88 g, 77.25 mmoles) and benzoyl peroxide (320 mg, 1.23 mmoles) was kept under reflux for 2 hours, then cooled, filtered and washed with a 10% $Na_2SO_3$ solution (200 ml), then with water, anhydrified and brought to dryness. The residue was taken up with 5% HCl (100 ml) and kept under reflux for 4 hours, then the solution was cooled, basified with NaOH, washed with ethyl acetate and slowly re-acidified to give a precipitate which was filtered, washed with water, dried on $P_2O_5$ under vacuum to give 6.43 g of the title compound (yield: 60%).

EXAMPLE 3

5,6-Dimethoxy-3-(triphenyl-$\lambda^6$-phosphanyl)-3H-isobenzofuran-1-one

A suspension of 2-formyl-4,5-dimethoxy-benzoic acid (6.43 g, 30.62 mmoles), obtained as described in example 2, triphenyl-phosphine (8.3 g, 30.62 mmoles), 30% HBr in acetic acid (8.26 ml, 30.62 mmoles) and glacial acetic acid (20 ml) under $N_2$ was heated at 90° C. for 4.5 hours. The mixture was brought to dryness, re-dissolved in acetonitrile (50 ml) and diluted with ethyl ether up to turbidity, then cooled and filtered, and the filtrate was washed with ethyl ether and dried under vacuum to give 13.6 g of the title compound (yield: 83%).

$^1$H-NMR (DMSO): 8.35 and 7.31 (2s,2H); 8.03–7.66 (m,15H); 6.01 (s,1H); 3.84 and 3.45 (2s,6H).

EXAMPLE 4

5,6-Dimethoxy-3-pyridin-4-ylmethylen-3H-isobenzofuran-1-one

Triethylamine (20 ml, 145 mmoles) was dropwise added to a suspension of 5,6-dimethoxy-3-(triphenyl-$\lambda^6$-phosphanyl)-3H-isobenzofuran-1-one (78 g, 145 mmoles), obtained as described in example 3, and 4-pyridincarboxaldehyde (13 ml, 145 mmoles) in $CH_2Cl_2$ (1 l), at room temperature under stirring. After 1.5 hours the mixture was filtered and evaporated and the residue was treated with ethanol under reflux, cooled and filtered. The mother liquors were chromatographed (eluent: 100% $CH_2Cl_2$, then with 1% $CH_3OH$) and the residue was brought to dryness and joined to the above filtrate to give 25 g of the title compound.

EXAMPLE 5

6,7-Dimethoxy-4-pyridin-4-ylmethyl-2H-phthalazin-1-one 5,6-Dimethoxy-3-pyridin-4-ylmethylen-3H-isobenzofuran-1-one (25 g, 88.34 mmoles), obtained as described in example 4, was reacted with hydrazine hydrate (500 ml) for 2 hours at room temperature under stirring, then for 1 hour under reflux. The mixture was diluted with water (300 ml), cooled and filtered to give 23 g of the title compound (yield: 87%).

EXAMPLE 6

1-Chloro-6,7-dimethoxy-4-pyridin-4-ylmethyl-phthalazine

A suspension of 6,7-dimethoxy-pyridin-4-ylmethyl-2H-phthalazin-1-one (10 g, 33.6 mmoles), obtained as described in example 5, in $POCl_3$ (70 ml) was heated at 90° C. for 4 hours. $POCl_3$ was evaporated and the residue dissolved in water, a saturated $NaHCO_3$ solution and NaOH up to obtain a precipitate which was filtered and re-suspended in $CH_3OH$, brought to dryness, re-suspended in acetone and filtered again. The residue was dried at 45° C. under vacuum to give 9.56 g of the title compound.

EXAMPLE 7

8,9-Methoxy-6-pyridin-4-ylmethyl-tetrazol[5.1-a] phthalazine (Compound 1)

$NaN_3$ (103 mg, 1.583 mmoles) was added to a solution of 1-chloro-6,7-dimethoxy-4-pyridin-4-ylmethyl-phthalazine (500 mg, 1.583 mmoles), obtained as described in example 6. in DMF (4.5 ml) and the mixture was heated at 80° C. for 16 hours. DMF was evaporated and the residue partitioned between water and $CH_2C_2$. The collected organic phases were anhydrified and brought to residue to give 420 mg of the title compound (yield: 82.3%).

$^1$H-NMR ($CDCl_3$): 8.55–8.52 (m, 2H); 8.00 (s, 1H), 7.25–7.22 (m, 3H); 4.59 (s, 2H); 4.10 and 3.90 (2s, 6H).

EXAMPLE 8

6-Methoxy-3H-isobenzofuran-1-one

Formaldehyde 48% v/v (65 ml, 0.86 moles) under stirring, then 3-methoxy-benzoic acid (100 g, 0.66 moles) were added to concentrated HCl (1 l) and the mixture was heated at 100° C. by checking the development of gas for 30 minutes. The cooling of the mixture brought to the formation of a precipitate which was filtered and put aside, while the mixture was washed with water, then with 5% NaOH. The new precipitate was extracted twice with $CH_2Cl_2$, the extract was anhydrified, concentrated, joined to the previously filtered solid, and both were dissolved in $CH_2Cl_2$ and treated with diethylamine (120 ml, 1.15 moles). After 24 hours it was extracted with 10% HCl and the phases were separated with $CH_2Cl_2$. The organic phase was washed with 10% NaOH, decoloured with charcoal, anhydrified and concentrated. The residue was dissolved in $CH_2Cl_2$ and treated, under stirring, with 10% HCl for 30 minutes. The organic phase was washed with water, anhydrified and concentrated. The residue was dissolved in $CH_2Cl_2$ and treated with 10% NaOH under stirring for 30 minutes. The organic phase was washed with water, dried and concentrated to give a solid which was crystallised from aqueous $CH_3OH$. The filtrate was dried at 50° C. on $P_2O_5$, then crystallised again from aqueous $CH_3OH$ to give 35.28 g of the title compound (yield: 32%).

$^1$H-NMR ($CDCl_3$): 7.37–7.20 (m, 3H); 5.21 (s, 1H); 3.85 (s, 3H).

EXAMPLE 9

3-Bromo-6-methoxy-3H-isobenzofuran-1-one

6-Methoxy-3H-isobenzofuran-1-one (35.28 g, 0.215 moles), obtained as described in example 8, suspended in $CCl_4$ (350 ml) under $N_2$, was added with N-bromo-succinimide (40 g, 0.225 moles). benzyl-peroxide in catalytic amount, then was slowly brought under reflux. After 2.5 hours the heating was stopped and the mixture was left standing overnight at room temperature. Further catalyst was added and it was heated for further 3.5 hours. The mixture was cooled in ice and filtered over celite by washing well with $CCl_4$, then concentrated to give 41 g of the title compound (yield: 78%).

$^1$H-NMR ($CDCl_3$): 7.50–7.25 (m, 4H); 3.87 (s, 3H).

EXAMPLE 10

(5-Methoxy-3-oxo-1,3-dihydro-isobenzofuran-1-yl) triphenylphosphonium bromide

Triphenyphosphine (42 g, 0.16 moles) was added to 3-bromo-6-methoxy-3H-isobenzofuran-1-one (41 g, 0.169 moles), obtained as described in example 9, suspended in anhydrous acetonitrile (205 ml) under $N_2$. The mixture was heated under reflux and after 3 hours cooled and concentrated to give a solid which was treated with ethyl ether, filtered and concentrated under vacuum. There were thus obtained 74 g of the title compound (yield: 84%).

$^1$H-NMR (CDCl$_3$): 9.63 (s, 1H), 7.84–7.75 (m, 15H); 7.09–6.91 (m, 3H); 3.77 (s, 3H).

EXAMPLE 11

3-(3,5-Dichloro-pyridin-4-ylmethylen)-6-methoxy-3H-isobenzofuran-1-one

Triethylamine (18.5 ml, 0.134 moles) was dropwise added to a suspension of (5-methoxy-3-oxo-1,3-dihydro-isobenzofuran-1-yl)triphenyl phosphonium bromide (74 g. 0.134 moles) obtained as described in example 10, and 3,5-dichloro-pyridin-4-carbaldehyde (23.6 g, 0.134 moles) in CH$_2$Cl$_2$ (500 ml) under N$_2$ by controlling the temperature with a water-bath. The mixture was kept under stirring overnight, then cooled and treated with 5% HCl. The phases were separated and the acid one was re-extracted with CH$_2$Cl$_2$, washed with water/NaCl, decoloured with charcoal, dried and concentrated under high vacuum. There were obtained 85.4 g of a crude which was used as such in the subsequent step. A sample of the crude was purified by flash chromatography (eluent:hexane/ethyl acetate 1:1).

$^1$H-NMR (CDCl$_3$): 8.60 (s, 2H); 7.77–6.68 (m, 4H); 3.80 (s,3H).

EXAMPLE 12

4-(3,5-Dichloro-pyridin-4-ylmethyl)-7-methoxy-2H-phthalazin-1-one

Hydrazine (18.4 ml, 0.378 moles) was added to a suspension of 3-(3,5-dichloro-pyridin-4-ylmethylen)-6-methoxy-3H-isobenzofuran-1-one (24.4 g, 0.126 moles), obtained as described in example 11, in CH$_3$OH (200 ml), under N$_2$. The mixture was heated under reflux for 1 hour, then kept overnight at room temperature, cooled in ice, and the solid was filtered, washed with very cold CH$_3$OH and dried in oven at 50° C. under vacuum, to give 33.3 g of the title compound (yield: 80%). m.p.: 259–262° C.

$^1$H-NMR (CDCl$_3$): 12.34 (s, 1H); 8.64 (s, 2H), 8.19–7.54 (m 3H); 4.58 (s, 2H); 3.95 (s, 3H).

EXAMPLE 13

4-Chloro-1-(3,5-dichloro-pyridin-4-ylmethyl)-6-methoxy-phthalazine

POCl$_3$ (22.2 ml, 230 mmoles) was added to a suspension of 4-(3,5-dichloro-pyridin-4-ylmethyl)-7-methoxy-2H-phthalazin-1-one (10 g, 25.5 mmoles), obtained as described in example 12, in acetonitrile (300 ml) and the mixture was heated under reflux. After 3 hours the solution was concentrated, taken up with CH$_2$Cl$_2$, with water, and the pH was brought to 7–8 with Na$_2$CO$_3$. The organic phases were decoloured with charcoal, dried and concentrated to give 10 g of the title compound (stoichiometric yield).

$^1$H-NMR (CDCl$_3$): 8.50 (s, 2H); 8.13–7.54 (m, 3H); 4.88 (s, 2H); 4.04 (s, 3H).

EXAMPLE 14

[4-(3,5-Dichloro-pyridin-4-ylmethyl)-7-methoxy-phthalazin-1-yl]-hydrazine

Hydrazine hydrate (0.81 ml, 0.84 g, 16.8 mmoles) was added to a solution under N$_2$ of 4-chloro-1-(3,5-dichloro-pyridin-4-ylmethyl)-6-methoxy-phthalazine (2 g, 5.6 mmoles), obtained as described in example 13, in ethanol (30 ml), and the mixture was kept under reflux for 24 hours, then cooled in ice and the resultant precipitate was filtered, washed with ethanol and ethyl ether and dried under vacuum at 50° C. to give 2.14 g of the title compound (stoichiometric yield). m.p.: 297–299° C.

$^1$H-NMR (DMSO/D$_2$O): 8.61 (s, 2H); 7.95–7.20 (m, 3H); 4.48 (s, 2H); 3.87 (s, 3H).

EXAMPLE 15

6-(3,5-Dichloro-pyridin-4-ylmethyl)-9-methoxy-3-methyl-[1,2,4]-triazole-[3,4-a]-phthalazine (Compound 2)

Acetic anhydride (0.2 ml. 0.22 g, 2.2 mmoles) was added to a suspension under N$_2$ of [4-(3,5-dichloro-pyridin-4-ylmethyl)-7-methoxy-phthalazin-1-yl]-hydrazine (0.7 g, 2 mmoles), obtained as described in example 14, in acetic acid, and the mixture was kept under reflux for 20 hours, then brought to small volume, taken up with CH$_2$Cl$_2$ and washed twice with 2.5% NaOH, then with water. The mixture was decoloured with charcoal, filtered over celite and concentrated under vacuum to give a solid which was triturated in ethyl ether to give 0.57 g of the title compound (yield: 77%). m.p.: 241.6–243.6° C.

$^1$H-NMR (CDCl$_3$): 8.55 (s, 2H); 8.06–7.34 (m, 3H); 4.76 (s, 2H); 4.03 (s, 3H); 2.46 (s, 3H).

EXAMPLE 16

6-(3,5-Dichloro-pyridin-4-ylmethyl)-9-methoxy-tetrazolo[5,1-a]-phthalazine (Compound 3)

NaN$_3$ was added to a solution under N$_2$ of 4-chloro-1-(3,5-dichloro-pyridin4-ylmethyl)-6-methoxy-phthalazine (1 g, 2.82 mmoles), obtained as described in example 13, in anhydrous DMF (20 ml) and the mixture was heated at 80° C. overnight, then at 120° C. for 7 hours, then poured into water (10 volumes) and extracted 3 times with CH$_2$Cl$_2$, dried and concentrated under vacuum to give a solid which was purified by flash chromatography (eluent:60:80 petrolatum/ethyl acetate 6:4). The eluate was crystallised from acetonitrile (75 ml) to give 0.36 g of the title compound (yield: 78.5%). m. p.: 275–276° C.

$^1$H-NMR (CDCl$_3$): 8.57 (s, 2H); 8.22 (d, 1H, JHH=8.7 Hz); 8.246 (d, 1H, JHH=2.5 Hz); 7.57 (dd, 1H); 4.89 (s, 2H); 4.10 (s, 3H).

EXAMPLE 17

5-(3,5-Dichloro-pyridin-4-ylmethyl)-8 -methoxy-1,3,3a,4-tetraaza-cyclopentan[a]naphthalene (Compound 4)

NaH (0.14 g, 3.38 mmoles) was added to a solution under N$_2$ of 1H-tetrazole (0.315 g, 4.5 mmoles) in anhydrous DMF (10 ml) and the mixture was kept under stirring for 2 hours. 4-Chloro-1-(3,5-dichloro-pyridin-4-ylmethyl)-6-methoxy-phthalazine (0.8 g, 2.25 mmoles), obtained as described in example 13, was added and it was heated at 80° C. then at 100° C. overnight. The mixture was poured into water and extracted with CH$_2$Cl$_2$. The organic phase containing an insoluble was concentrated under vacuum and taken up with CH$_3$OH. A solid was obtained which, triturated with hot CH$_3$OH then cooled, was removed by filtration. The mother liquors were brought to dryness to give a solid which was flash chromatographed (eluent: CH$_2$Cl$_2$/CH$_3$OH 98:2), to yield a solid which, triturated with ethyl ether, gave 0.18 g of the title compound (yield: 22%). m.p.: 231.3–232.3° C. (dec.).

$^1$H-NMR (CDCl$_3$): 8.77 (s, 1H); 8.56 (s, 2H); 8.09–8.03 (m, 2H), 7.40 (dd, 1H, JHH=9 Hz, J2HH=2.7 Hz); 4.76 (s, 2H); 4.04 (s, 3H).

EXAMPLE 18
Evaluation of the PDE 4 Enzyme Inhibition
a) Purification of Human Polymorphonucleate Leukocytes The polymorphonucleate leukocytes (PMNs) were isolated from peripheral blood of healthy volunteers according to what described by Boyum A., Scand. J. Immunol., 1976, 5th suppl., 9). Shortly, the isolation of the PMNs was effected by Ficoll-Paque gradient centrifugation followed by sedimentation on dextrane and the erythrocyte contamination was eliminated by hypotonic lysis.

b) PDE 4 Enzyme Purification

The human PMNs were re-suspended in TRIS/HCl buffer (10 mM pH 7.8) containing MgCl$_2$ (5 mM), EGTA (4 mM), mercaptoethanol (5 mM), TRITON-X100 (1%), pepstatin A (1 μM), PMSF (100 μM) and leupeptin (1 μM), and homogenised by Polytron. The homogenate was centrifuged at 25.000×g for 30 minutes at 4° C. and the supernatant was used for the PDE 4 enzyme purification by ion exchange chromatography using the FPLC technique according to what described by Schudt C. et al., Naunyn-Schmidberg's Arch. Pharmacol., 1991, 334, 682. The supernatant was seeded on an UNO Q12 column (Bio-Rad) and the enzyme was eluted by sodium acetate gradient from 50 mM to 1M. The fractions containing enzymatic activity were collected, dialysed against water and concentrated. The resulting PDE 4 enzyme was stored at −20° C. in the presence of ethylenglycole (30%, v/v) until the use.

c) PDE 4 Enzyme Inhibition

The enzyme activity was evaluated with an Amersham kit based on the SPA (Scintillation Proximity Assay) technique. The enzymatic reaction was effected in a total volume of 100 μl of TRIS/HCl buffer (50 mM, pH7.5). MgCl$_2$ (8.3 mM), EGTA (1.7 mM). cAMP (1 μM) and [$^3$H]cAMP (~100.000 dpm) as tracer. The compounds of the invention were added at the selected concentrations. The reaction was started by adding the enzyme (15 μg protein/ml), went on for 40 minutes at 30° C. and stopped by adding 50 μl of suspension of SPA particles. The radioactivity due to the particles was measured in a emitting counter. The results are expressed as percent activity versus the control present in each experiment. The IC$_{50}$ values were calculated over 9 equidistant concentrations in logarithmic scale using a 4-parameters logistic function by software. The compounds of the present invention showed to selectively inhibit PDE 4: for example. Compound 2 gave a value of IC$_{50}$=207 nM.

What is claimed is:

1. A compound of formula (I)

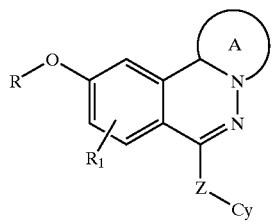

(I)

wherein
A is a 5–7 membered heterocycle having from 1 to 4 nitrogen atoms, optionally partially or totally unsaturated, and optionally substituted by a (C$_{1-4}$)alkyl group in turn optionally substituted;

Z is NH, methylene, a C$_{2-6}$ alkylene chain optionally branched and/or unsaturated and/or interrupted by a C$_{5-7}$ cycloalkyl residue;

Cy is phenyl or heterocycle optionally substituted by one or more substituents, or a COR$_4$ group wherein R$_4$ is hydroxy, alkoxy, amino optionally substituted by one or two (C$_{1-6}$)alkyl groups or by hydroxy;

R is a (C$_{1-6}$)alkyl or polyfluoro(C$_{1-6}$)alkyl group;

R$_1$ is hydrogen; a (C$_{1-8}$)-alkyl, (C$_{2-8}$)-alkenyl or (C$_{2-8}$)-alkynyl group optionally substituted by hydroxy, oxo, aryl or heterocycle, and optionally interrupted by one or more heteroatoms or heterogroups; a (C$_{1-4}$)alkoxy group or a (C$_{4-7}$)cycloalkoxy group optionally having an oxygen atom and optionally substituted by a polar substituent in the cyclic moiety, aryloxy, aryl-(C$_{1-10}$)-alkoxy wherein the polar substituent is selected from the group consisting of a hydroxy and keto group;

the N→O derivatives of the compounds of formula I and the pharmaceutically acceptable salts thereof.

2. The compound according to claim 1 wherein Z is methylene or a C$_{2-6}$ alkylene chain.

3. The compound according to claim 1 wherein Z is methylene or a C$_{2-6}$ alkylene chain; and
Cy is a heterocycle optionally substituted by one or more substituents.

4. The compound according to claim 1 wherein Z is methylene; and Cy is pyridine substituted by two substituents.

5. A process for the preparation of the compound according to claim 1 wherein Z is other than NH, comprising
reacting an acid of formula (II)

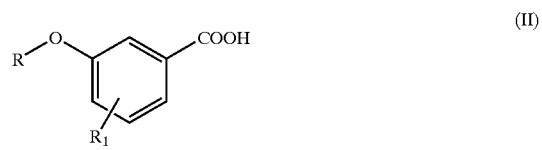

(II)

wherein R and R$_1$ are as defined in claim 1, with formaldehyde/HCl to produce a compound of formula (III)

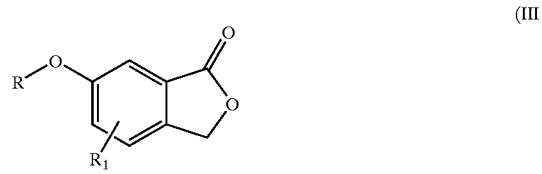

(III)

wherein R and R$_1$ are as above defined,
oxidizing and hydrolyzing the compound of formula (III) to produce a compound of formula (IV)

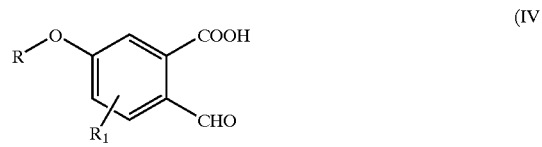

(IV)

wherein R and R$_1$ are as above defined, contacting the compound of formula (IV) with a hydrohalogenidric acid and triphenylphosphine to produce a compound of formula (V)

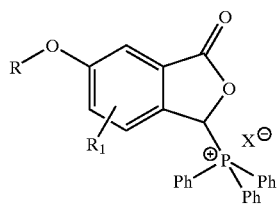
(V)

wherein R and R$_1$ are as above defined, contacting said compound of formula V with an aldheyde of formula (VI)

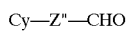
(VI)

in the presence of an organic base wherein Cy is as defined in claim 1 and Z" may or may not be present with the proviso that when Z" is present Z" is a C$_{1-5}$ alkylene chain optionally branched and/or unsaturated and/or interrupted by a C$_{5-7}$ cycloalkyl residue, to produce a compound of formula (VII)

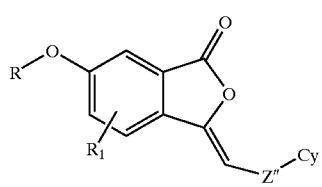
(VII)

wherein R, R$_1$, Z" and Cy are as above defined, contacting the compound of formula (VII) with hydrazine to produce a compound of formula (VIII)

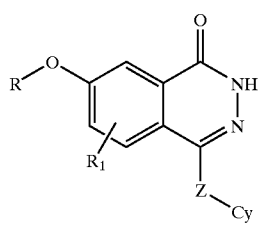
(VIII)

wherein R, R$_1$ and Cy are as above defined and Z is as defined in claim 1 with the proviso that Z is not amino, contacting the compound of formula (VIII) with a halogenating agent to produce a compound of formula (IX)

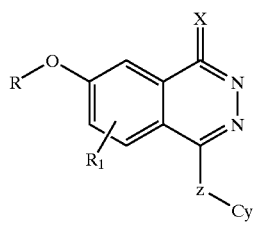
(IX)

wherein R, R$_1$ and Cy are as above defined, and X is chlorine or bromine, and contacting the compound of formula (IX) with a suitable nucleophile or with hydrazine and then contacting with a suitable acylating agent to produce the compound of formula (I),

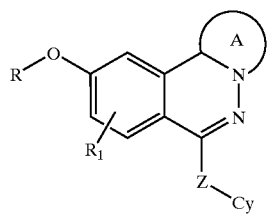
(I)

wherein R, R$_1$, Z, Cy, and A are as defined in claim 1.

6. A pharmaceutical composition, comprising a therapeutically effective amount of the compound according to claim 1 in admixture with a suitable carrier.

7. A process for the preparation of the compound according to claim 1 wherein Z is other than NH, comprising reacting an acid of formula (II),

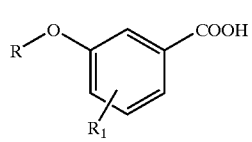
(II)

wherein R and R$_1$ are as defined in claim 1, with formaldehyde/HCl to produce a compound of formula (III)

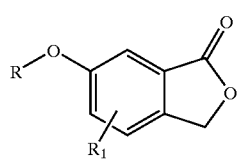
(III)

wherein R and R$_1$ are as above defined, radicalic halogenating the compound of formula (III) to produce a compound of formula (IIIa)

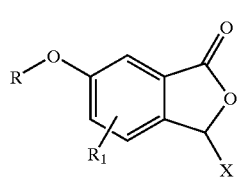
(IIIa)

wherein R and R$_1$ are as above defined, and X is chlorine or bromine, contacting the compound of formula (IIIa) with triphenylphosphine to produce a compound of formula (V)

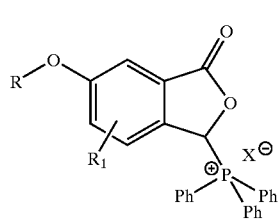
(V)

wherein R and R$_1$ are as above defined, contacting said compound of formula V with an aldheyde of formula (VI)

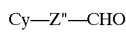

Cy—Z″—CHO    (VI)

in the presence of an organic base wherein Cy is as defined in claim 1 and Z″ may or may not be present with the proviso that when Z″ is present Z″ is a $C_{1-5}$ alkylene chain optionally branched and/or unsaturated and/or interrupted by a $C_{5-7}$ cycloalkyl residue, to produce a compound of formula (VII)

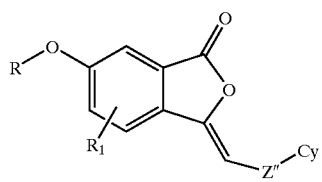

(VII)

wherein R, $R_1$, Z″ and Cy are as above defined, contacting the compound of formula (VII) with hydrazine to produce a compound of formula (VIII)

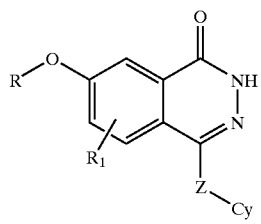

(VIII)

wherein R, $R_1$ and Cy are as above defined and Z is as defined in claim 1 with the proviso that Z is not amino, contacting the compound of formula (VIII) with a halogenating agent to produce a compound of formula (IX)

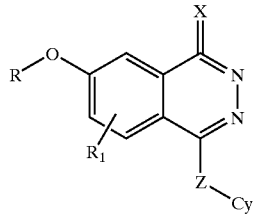

(IX)

wherein R, $R_1$ and Cy are as above defined, and X is chlorine or bromine, and contacting the compound of formula (IX) with a suitable nucleophile or with hydrazine and then contacting with a suitable acylating agent to produce the compound of formula (I),

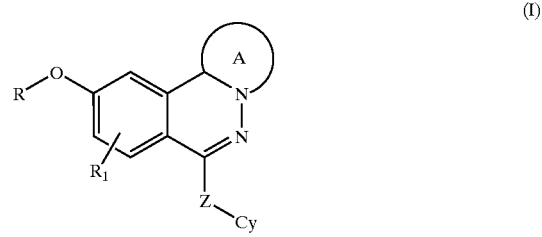

(I)

wherein R, $R_1$, Z, Cy, and A are as defined in claim 1.

8. A method of treating, reducing, arresting, or alleviating allergic or inflammatory pathologies in a patient, comprising administering the compound according to claim 1 to a patient in need thereof.

9. A method of treating, reducing, arresting, or alleviating the symptoms of allergic or inflammatory pathologies in a patient, comprising administering the compound according to claim 1 to a patient in need thereof.

10. A method of treating, reducing, arresting, or alleviating respiratory diseases in a patient, comprising administering the compound according to claim 1 to a patient in need thereof.

11. A method of treating, reducing, arresting, or alleviating the symptoms of respiratory diseases in a patient, comprising administering the compound according to claim 1 to a patient in need thereof.

12. A method of reducing the activity of PDE 4, comprising contacting the compound according to claim 1 with a PDE 4, wherein the PDE 4 has an elevated activity relative to the activity of the PDE 4 in the presence of the compound.

13. A method, comprising contacting the compound according to claim 1, with a suitable carrier.

* * * * *